United States Patent [19]

Lim et al.

[11] Patent Number: 5,302,628
[45] Date of Patent: Apr. 12, 1994

[54] DENTURE ADHESIVE COMPOSITION

[75] Inventors: Richard Lim, Livingston; Robert Leone, Fanwood, both of N.J.

[73] Assignee: Block Drug Company, Inc., Jersey City, N.J.

[21] Appl. No.: 829,220

[22] Filed: Feb. 3, 1992

[51] Int. Cl.$^5$ .............................................. A61K 6/00
[52] U.S. Cl. ................................... 523/105; 523/118; 523/120; 524/366; 524/377; 524/379; 524/503; 433/180
[58] Field of Search ................... 523/105, 118, 120; 524/366, 379, 377, 503, 522; 433/180

[56] References Cited

U.S. PATENT DOCUMENTS

| | | | |
|---|---|---|---|
| 4,373,036 | 2/1983 | Chang et al. | 523/120 |
| 4,542,168 | 9/1985 | Chang et al. | 523/120 |
| 4,647,600 | 3/1987 | Kawahara et al. | 523/116 |
| 5,011,868 | 4/1991 | Keegan | 523/120 |

FOREIGN PATENT DOCUMENTS 0346097 12/1989 European Pat. Off. .

Primary Examiner—Paul R. Michl
Assistant Examiner—LaVonda Dewitt
Attorney, Agent, or Firm—Ostrolenk, Faber, Gerb & Soffen

[57] ABSTRACT

A denture adhesive which is useful in aiding in the retention of dentures to the oral mucosa constitutes a mixture of polyacrylic acid and hydroxy compound of sufficiently high molecular weight to be solid at room temperature. The combination can be used in the form of a powder or can be mixed in an oil base for application as a cream or liquid. The composition can also include hydration enhancers and pH adjustment agents.

17 Claims, No Drawings

DENTURE ADHESIVE COMPOSITION

BACKGROUND OF THE INVENTION

Denture adhesives are employed for the purpose of assisting the adherence of dentures to the oral mucosa. Such adhesives are usually formulated either as anhydrous powders or as cream based formulations. Both types acquire moisture from saliva to hydrate the formulation in such a way to form a thin film between the denture and oral mucosa and to develop their useful properties. A high degree of tack is essential for the adhesive to function properly and equally important is the cohesive strength of the hydrated denture adhesive. A high degree of strength helps to prevent loss of adhesion of the denture to the oral mucosa.

Another important characteristic of a denture adhesive is the rate of hydration. Only after the adhesive becomes fully hydrated does it become fully effective. Not only do the polymers and/or gums employed play an important role in determining the rate of hydration but also the form of the adhesive is significant. Thus, for example, a powder adhesive can hydrate faster than a cream. The rate of hydration further affects the smoothness and overall mouth feel of the denture adhesive. Moreover, it is apparent that part of the adhesive will be between the denture and the gums and will therefore not have access to the moisture because it is out of direct contact with the saliva. It is therefore important that a denture fixative composition have the characteristic of becoming hydrated evenly throughout so that its strength is evenly distributed. As a result, various polymers and gums have been used heretofore for the specific purpose of promoting adhesion. While these hydration adjuvants may not contribute to the tack and strength of the denture adhesive, they are useful in assisting in water pick up.

Polyacrylic acid has been employed in numerous pharmaceutical formulations in order to exploit its thickening, suspending and emulsifying capabilities. It has been used also in denture adhesive formulations. For example, U.S. Pat. No. 4,373,036 teaches the use of polyacrylic acid with neutralizing agents and cross-linkers in a denture adhesive formulation which can also include hydroxypropyl cellulose and polyethylene oxide. However it cannot be used alone because, as is known, a partially or wholly neutralized polyacrylic acid generates a gel in aqueous systems which has a low cohesive strength and a structure which may easily be ruptured when subjected to stresses such as those which occur during mastication.

Polyvinyl alcohol is a water soluble polymer which can form a highly viscous gel in water. It has been used as a thickener, emulsifier, adhesive and coating. U.S. Pat. No. 4,880,702 teaches the use of polyvinyl alcohol in a three layer composition for stabilizing dentures alone or in combination with polyethylene oxide, sodium carboxymethyl cellulose or microcrystalline wax. The polyvinyl alcohol is cast into a thin film which is used in the outer layers of the composition and becomes tacky when hydrated in the mouth.

Polyalkylene oxides such as polyethylene oxide and polypropylene oxide have been widely used as solvents, lubricants, surfactants and in pharmaceutical and cosmetic bases. They have also been used in a denture adhesive composition containing, inter alia, cellulose ethers, an alkali metal salt of carboxymethyl cellulose and a hydrocarbon base (EP 140,486). Polyethylene glycol has been used in denture adhesives as taught for instance in U.S. Pat. Nos. 4,530,942, 4,522,956, 4,521,551, 4,514,528 and 4,474,902. Polypropylene glycol has been used in conjunction with polyvinyl acetate and other natural gums in U.S. Pat. No. 4,804,412.

Chang et al. in U.S. Pat. Nos. 4,470,814 and 4,542,168 teach a denture fixative composition containing as the fixative, a partially neutralized and crosslinked polyacrylic acid or a precursor combination of the polyacrylic acid, neutralizing agent and crosslinking agent adapted to form the active fixative, and at least one hydrophilic polymer which is preferably sodium carboxymethyl cellulose, hydroxypropyl guar or sodium alginate. The crosslinking agents are the dentally acceptable salts, oxides and bases of divalent cations and/or polyhydroxy compounds such as glycerin, propylene glycol, ethylene glycol, tetramethylene glycol and the like.

It is known that polyacrylic acid and compounds containing hydroxyl functionality interact. A combination of the two materials does result in a mixture with a higher viscosity than either of the compounds alone and when this occurs, a highly viscous and gummy material is obtained. That property is advantageous when the combination is used as a denture adhesive but the same property also introduces an element of difficulty in applying the denture adhesive onto the dentures. It is desirable that the denture adhesive be applied as a thin layer on the denture in order to provide for an even distribution of the adhesive and a comfortable fit. Development of a viscous and gummy consistency when the two compounds are mixed makes the even application of the denture adhesive more difficult.

It is accordingly the object of this invention to provide a new denture adhesive composition which hydrates more evenly, and develops high tack and superior cohesive strength and which can be more easily applied to a denture. This and other objects of the invention will become apparent to those of ordinary skill in this art from the following detailed description.

SUMMARY OF THE INVENTION

This invention relates to an oral composition which is used to aid in the retention of dentures to the oral mucosa. More particularly it relates to a denture adhesive composition which comprises a combination of a solid polyacrylic acid and a hydroxyl functional compound of sufficiently high molecular weight to be a solid at room temperature. The composition can also contain hydration adjuvants, pH adjustment agents, flavors, preservatives, coloring and the like and can take the form of a powder or can be blended with mineral oil and petrolatum to form a cream or liquid formulation. After being applied to the denture and upon coming into contact with saliva, hydration occurs quickly developing a high degree of tack and cohesive strength.

DETAILED DESCRIPTION OF THE INVENTION

In accordance with the present invention, a denture fixative composition in powder, liquid or cream form is provided which can develop a high degree of tack and uniform viscous mucilages with high cohesive strength when spread over the denture-mucosa interface and contacted with saliva, thereby providing superior denture adhesive properties. The adhesive is an anhydrous mixture of solid polyacrylic acid and a polyhydroxy compound of sufficiently high molecular weight to be a solid at room temperature. The composition can, and preferably does, contain hydration adjuvants and a pH adjustment agent.

The polyacrylic acid and hydroxy functional compound individually form highly viscous gels in water. However when more water is added, these gels also rapidly dissolve. The combination of the two resins produces a hydrogen bonding complex which has a viscosity higher than either of the two resins alone and the complex has a higher strength and better resistance to dissolution in water. The invention avoids the difficulty of uneven application of the denture adhesive produced by the viscous and gummy properties of the combination by preventing interaction of the polymers before the composition is applied to the dentures. This requires that the polyacrylic acid and the polyhydroxy functional compound are solids, possibly being blended in an anhydrous base. The solid form of the ingredients prevents interaction until the denture adhesive is applied to the denture and put in the mouth where water from the saliva causes hydration. At this point, the polymers interact and the properties of a viscous and tacky material are produced in the mouth. The combination of the present invention also provides a denture adhesive having a higher cohesive strength.

The polyacrylic acid is well known and is available commercially from numerous companies. Examples of these materials would be polyacrylic acid commercially available from B. F. Goodrich Co. under the product names Carbopol ® and Noveon TM. Such polyacrylic acids generally have molecular weights of about 500,000 to 5,000,000 and preferably about 2,000,000 to 4,000,000. Preferably the commercially available cross-linked polyacrylic acids which have a viscosity of about 3,000 to 80,000 centipoises for a 0.5% neutralized aqueous solution are employed. Most preferably, the polyacrylic acid has a viscosity of about 30,000 to 40,000 cps.

The hydroxy functional polymer used in the present invention can be one or more polyalkylene oxides or polyalkylene glycols or polyvinyl alcohols or the like. The molecular weight of the polymer is sufficiently high that it is a solid at room temperature.

The polyvinyl alcohol used in the present invention generally has a degree of hydrolysis, i.e. the percentage of acetate groups which have been hydrolyzed from the polyvinyl acetate precursor, of about 5% to 100%. These polymers have a viscosity of about to 70 cps when measured in a 4% aqueous solution. The preferred grade of polyvinyl alcohol has a degree of hydrolysis of 65 to 89% and a viscosity of 6 to 60 cps, and particle size smaller than 210 μm. Examples are Airvol ® 540-S from Air Products and Gohsenol ® KP-08 from Nippon Gohsei.

The polyalkylene glycols include such materials as polyethylene glycol and polypropylene glycol, both of which are commercially available. Examples include polyethylene glycol E3350NF made by Dow Chemical Co. and Carbowax ® 8000 made by Union Carbide Corp. The molecular weight generally varies from about 200 to 20,000. Of the polyalkylene glycols, polyethylene glycol is preferred. The polyalkylene oxides include polyethylene oxide, polypropylene oxides and copolymers of ethylene oxide and propylene oxide. The copolymers are commercially available in a large variety of ratios of propylene to ethylene functional groups.

The alkylene units in the polyalkylene oxides and glycols generally contain 2 to about 4 carbon atoms.

The polyacrylic acid and the hydroxyl functional polymers are preferably employed in the form of finely divided powders. Each generally has a particle size smaller than 210 μm and most preferably has a particle size smaller than 150 μm.

The relative proportions of the polyacrylic acid and hydroxy polymer are generally in a weight ratio that will provide the most advantageous properties to the denture adhesive composition. This ratio can vary over a considerable range depending on the particular combination being employed. Generally the weight ratio is about 1:0.25 to 1:8 and preferably about 1:1 to 1:4.

The denture adhesive of the invention preferably contains a hydration adjuvant. These are hydrophilic polymers which assist in the hydration of the composition and also impart a more acceptable mouth feel to the composition. Among the hydrophilic polymers that can be used are cellulose derivatives such as hydroxymethyl cellulose, hydroxyethyl cellulose, hydroxypropyl cellulose and the like, natural gums such as karaya gum, guar, alginic acid, xanthan gum and other polymers such as hydroxy propyl guar and sodium alginate.

The addition of an alkaline material to the composition is preferred in order to adjust the pH so that it is more acceptable to the oral environment. Typical pH adjustment agents include calcium carbonate, calcium hydroxide, sodium carbonate and bicarbonate, zinc oxide, magnesium oxide and magnesium hydroxide. The alkaline salt is generally used in an amount sufficient to establish a pH of about 4.5 to 8 and preferably about 5.4 to 6.5.

In the preferred composition of polyacrylic acid, room temperature solid polyhydroxy compound, hydration adjuvant and pH adjustment agent, an adhesive effective amount of the polyacrylic acid is generally about 5 to 25%, preferably 7 to 20%, an adhesive effective amount of the polyhydroxy compounds about 10 to 60%, preferably 12 to 30%, the hydration adjuvants about 5 to 30%, preferably about 7 to 25% and the pH adjustment agent is of an amount sufficient to establish a pH of 4.5 to 8.

The adhesive composition can also contain a variety of dentally acceptable excipient materials conventionally used in the art. Among these can be mentioned flavoring agents, coloring agents, preservatives, thickeners, non-toxic anti-caking agents such as silica, magnesium stearate, talc, dicalcium phosphate and the like and for cream or liquid formulations, an anhydrous vehicle such as petrolatum and/or mineral oil. The denture adhesive, i.e. combination of solid polyacrylic acid and polyhydroxy compound, will generally be about 10 to 90% of the denture fixative composition and preferably about 20 to 85%.

Various examples are set forth below in order to illustrate the present invention. In these, as throughout this specification and claims, all parts and percentages are by weight and all temperatures are in degrees centigrade unless otherwise indicated.

EXAMPLE 1

The following ingredients are blended together to form a denture adhesive cream:

| Ingredient | Weight % |
| --- | --- |
| Polyacrylic acid | 10% |

-continued

| Ingredient | Weight % |
| --- | --- |
| Polyvinyl alcohol (88% Hydrolyzed) | 20% |
| Polyethylene oxide | 5% |
| Polyethylene glycol (MW 8,000) | 7% |
| Hydroxyethyl cellulose | 7% |
| Magnesium hydroxide | 2% |
| Mineral Oil | 30.5% |
| Petrolatum | 18% |
| Flavor, Color and Preservative | 0.5% |

EXAMPLE 2

A denture adhesive cream was prepared by blending the following ingredients together:

| Ingredient | Weight % |
| --- | --- |
| Polyacrylic acid | 11% |
| Polyvinyl alcohol (88% hydrolyzed) | 21% |
| Polyethylene oxide | 6% |
| Hydroxyethyl cellulose | 9% |
| Magnesium hydroxide | 2% |
| Mineral Oil | 30.5% |
| Petrolatum | 20% |
| Flavor, Color and Preservative | 0.5% |

EXAMPLE 3

A denture adhesive cream may be prepared by blending the following ingredients together:

| Ingredient | Weight % |
| --- | --- |
| Polyacrylic acid | 20% |
| Polyethylene glycol (MW 3350) | 12.5% |
| Polyethylene oxide | 10% |
| Xanthan Gum | |
| Sodium Bicarbonate | 1.5% |
| Mineral Oil | 26.5% |
| Petrolatum | 17.0% |
| Flavor, Color and Preservative | 0.5% |

EXAMPLE 4

A denture adhesive cream may be prepared by blending the following ingredients together:

| Ingredient | Weight % |
| --- | --- |
| Polyacrylic acid | 15% |
| Polyvinyl alcohol (88% hydrolyzed) | 23% |
| Hydroxypropyl cellulose | 10% |
| Sodium Bicarbonate | 1.5% |
| Mineral Oil | 30% |
| Petrolatum | 20% |
| Flavor, Color and Preservative | 0.5% |

EXAMPLE 5

A denture adhesive powder was prepared from the following ingredients all of which were used in the form of a powder whose particle size was smaller than 150 μm.

| Ingredient | Weight % |
| --- | --- |
| Polyacrylic acid | 20% |
| Polyvinyl alcohol | 35% |
| Polyethylene glycol (MW 8,000) | 15% |
| Polyethylene oxide | 10% |
| Hydroxyethyl cellulose | 18% |
| Magnesium hydroxide | 2% |

EXAMPLE 6

Comparative

A lap shear test was used in order to evaluate the strength and cohesiveness of the denture adhesive. In this test, the properties of the denture adhesive of Example 1 above were compared to the denture adhesive of Example 4 in Chang et al. U.S. Pat. No. 4,478,814. When the denture adhesive was mixed with water, the Chang prior art denture adhesive had a lap shear test result of 130 grams while the adhesive of Example 1 had a value of 645 grams. The denture adhesive of this invention was, therefore, significantly more cohesive.

EXAMPLE 7

Comparative

The denture adhesive cream of Example 1 had a viscosity of 1,300,000 centipoises. A second adhesive cream was prepared using the same formulation but substituting a liquid polyethylene glycol (MW 300) for the solid polyethylene glycol (MW 8,000). The resulting formulation when mixed was so viscous that it could not be measured by the Brookfield viscometer. This dramatic difference in viscosity illustrates the importance of using a solid polyhydroxy compound.

Various changes and modifications can be made in the products and process of this invention without departing from the spirit and scope thereof. The various embodiments which have been disclosed herein were for the purpose of further illustrating the invention but were not intended to limit it.

What is claimed is:

1. A denture adhesive which comprises an anhydrous combination of solid polyacrylic acid and polyhydroxy compound having a sufficient molecular weight to be solid at room temperature wherein said polyhydroxy compound is selected from the group consisting of polyalkylene glycol polymer, polyvinyl alcohol and combinations thereof.

2. The denture adhesive of claim 1 containing a hydration adjuvant and a pH adjustment agent.

3. The denture adhesive of claim 1 further comprising polyalkylene oxide.

4. The denture of claim 2 in which the polyacrylic acid is about 5 to 25%, the polyhydroxy compound is about 10 to 60%, the hydration adjuvant is about 5 to 30% and the pH adjustment agent is of an amount sufficient to establish a pH of 4.5 to 8.

5. The denture adhesive of claim 4 in which the polyacrylic acid is about 7 to 20%, the polyhydroxy compound is about 12 to 30% and the hydration adjuvant is about 7 to 25%.

6. The denture adhesive of claim 1 in the form of a powder whose particles are smaller than 210 μm.

7. The denture adhesive of claim 6 in which the particles are smaller than 150 μm.

8. A denture fixative which comprises an anhydrous combination of a dentally acceptable excipient and an effective fixative amount of the denture adhesive of claim 1.

9. The denture fixative of claim 6 containing a hydration adjuvant and a pH adjustment agent.

10. The denture fixative of claim 9 in which the polyhydroxy compound is at least one member selected from the group consisting of polyalkylene glycol and polyvinyl alcohol.

11. The denture fixative of claim 9 in which the polyacrylic acid is about 5 to 25%, the polyhydroxy compound is about 10 to 60%, the hydration adjuvant is about 5 to 30% and the pH adjustment agent is of an amount sufficient to establish a pH of 4.5 to 8.

12. The denture fixative of claim 11 in which the polyacrylic acid is about 7 to 20%, the polyhydroxy compound is about 12 to 30% and the hydration adjuvant is about 7 to 25%.

13. In a method of adhering dentures to oral mucosa employing a denture adhesive which spreads over the denture-mucosa interface to fill the gaps therebetween, the improvement which comprises employing the denture adhesive of claim 1 a said denture adhesive.

14. In a method of adhering dentures to oral mucosa employing a denture adhesive which spreads over the denture-mucosa interface to fill the gaps therebetween, the improvement which comprises employing the denture adhesive of claim 2 as said denture adhesive.

15. In a method of adhering dentures to oral mucosa employing a denture adhesive which spreads over the denture-mucosa interface to fill the gaps therebetween, the improvement which comprises employing the denture adhesive of claim 3 as said denture adhesive.

16. In a method of adhering dentures to oral mucosa employing a denture adhesive which spreads over the denture-mucosa interface to fill the gaps therebetween, the improvement which comprises employing the denture adhesive of claim 4 as said denture adhesive.

17. In a method of adhering dentures to oral mucosa employing a denture fixative which spreads over the denture-mucosa interface to fill the gaps therebetween, the improvement which comprises employing the denture fixative of claim 8 as said denture fixative.

* * * * *